United States Patent [19]

Brown et al.

[11] Patent Number: 4,529,582

[45] Date of Patent: Jul. 16, 1985

[54] TITRATION OF GROUP C STREPTOCOCCAL ANTIBODY

[75] Inventors: Karen K. Brown, Kansas City, Mo.; Sharon A. Bryant, Shawnee, Kans.

[73] Assignee: Miles Laboratories, Inc., Elkhart, Ind.

[21] Appl. No.: 454,908

[22] Filed: Dec. 30, 1982

[51] Int. Cl.$^3$ .................... A61K 49/00; G01N 33/48; G01N 33/54
[52] U.S. Cl. ......................................... 424/9; 424/88; 436/536; 436/538; 436/543
[58] Field of Search ............... 436/537, 538, 536, 543; 424/9, 88

[56] References Cited

U.S. PATENT DOCUMENTS 3,940,475  2/1976  Gross ................................... 436/537
4,277,437  7/1981  Maggio ............................... 436/537

FOREIGN PATENT DOCUMENTS 0623865  9/1978  U.S.S.R. ................................. 424/9

OTHER PUBLICATIONS

Bisno, Infec. Immun., 26 (1979), 1172-6.
Peterson et al., J. Infect. Dis., 139 (1979), 575-585.
Fischetti et al., J. Exp. Med., 144 (1976), 32-51.
Lancefield, J. Exp. Med., 67 (1938), 25-40.
Lancefield, J. Exp. Med., 106 (1957), 525-544.

*Primary Examiner*—Christine M. Nucker
*Attorney, Agent, or Firm*—James A. Giblin

[57] ABSTRACT

Group C streptococcal antibody levels in a serum sample can be determined via passive protection test in susceptible animals. Test is based on property of protective antibody in the serum sample to reduce the virulence of a group C streptococcal challenge and provides a means for detecting whether an animal (e.g. horse) is susceptible to infection by group C streptococcal organism.

4 Claims, No Drawings

TITRATION OF GROUP C STREPTOCOCCAL ANTIBODY

RELATED APPLICATION

Application Ser. No. 454,906, filed of even date herewith in the names of K. K. Brown and S. A. Bryant and entitled Determining Potency of Streptococcal Preparations.

BACKGROUND OF THE INVENTION

1. Field

This disclosure is concerned generally with an assay for antibodies to streptococcal organisms and specifically with a novel method of determining the titer of group C streptococcal antibodies in a blood serum sample.

2. Prior Art

Organisms of the genus Streptococcus include a variety of nonmotile, chiefly parasitic, gram-positive bacteria that divide only in one plane, occur in pairs or chains but not packets, and include important pathogens of man and domestic animals. The streptococcal genus has been divided into eight distinct groups labelled A, B, C, D, F, G, H, and K. This disclosure is generally concerned with group C streptococcal organisms.

A very important group C organism, *Streptococcus equi*, is the causitive agent of a severe respiratory disease of horses referred to as "Strangles". The disease is endemic in most parts of the world and epidemic in the United States. Race and show horses are particularly susceptible to repeated infections due to the stress of travel and exposure to new contacts. The disease begins with a mucopurulent nasal discharge, temperatures of 103°–106° F. and severe inflammation of the upper respiratory mucosa. It finally progresses to lymphadenitis and abscess formation which is sometimes severe enough to restrict air intake and cause suffocation of the animal. Strangles results in extensive loss of condition (loss of weight) as it often runs a course of 4–6 weeks. It is thought that there is a single strain of *Streptococcus equi* (a Lancefield Type C Strep.) which is responsible for this disease world-wide. See, for example, Bergy's Manual of Determinitive Bacteriology (8th Edition), p. 498 (1974). The only other known susceptible animal is the mouse.

Because of the debilitating and in some cases lethal effects of streptococcal infections in man and other animals, attempts have been made over the years to prepare streptococcal bacterins or bacterin-like preparations which could be used for vaccination purposes. Unfortunately, streptococcal strains tend to be very reactive and it has been noted that certain human streptococcal vaccines (in Groups A and B) have stimulated heart muscle reactions while Group C *Strep. equi* preparations, in live or inactivated forms, have been noted for their affinity for dermal tissue, producing severe swelling at the injection site. This known reactivity has tended to discourage the commercial use and development of immunizing streptococcal products for man and other animals.

In efforts to produce efficacious vaccines from group C streptococci in general, and with *Streptococcus equi* in particular, it is important to have available a serological assay to measure the titer of serum antibodies to the group C streptococcal organisms. Unfortunately, no such assay has been available.

It is known that human streptococcal literature describe a bactericidal plate count test to measure human streptococcal antibody levels. See for example, Bisno, Alan L., Infect. Immun. 26, 1172–1176 (1979) and Peterson, Phillip K. et al, J. Infect. Dis. 139, 575–585 (1979). That test relies on complement found in fresh human blood. A similar test has been used by J. B. Woolcock (Infection and Immunity, July 1974, p. 116–122) in determining presence or absence of antibody in rabbits and horses after vaccination with *Strep. equi*. However, the above test (including numerous modifications) was unable to provide a reproducible quantitative measurement of *Strep. equi* antibody in our experiments. Other serological assays have been described which include a long chain test (see Woolcock et al cited above) and various immunodiffusion tests (Fischetti, V. A. et al, The Journal of Experimental Medicine, Vol. 144, 1976 p. 32–51). Once again, attempts to develop these tests into quantitative serological assays related to protective antibody were unreliable. The above difficulties posed a major problem in the attempt to develop a safe, effective and non-reactive *Strep. equi* preparation that could be used to immunize horses since, without an accurate serological assay, there was no way to detect susceptible animals.

Quite surprisingly, we were able to show that a relatively simple passive protection test could be used to actually quantitate serological antibody in a susceptible animal such as the mouse. Details of our test are given below.

SUMMARY OF THE INVENTION

Our serological assay for determining the levels of group C streptococcal antibodies in a serum sample is based on the ability of protective antibody in the serum sample, if any, to passively reduce the virulence of a *Strep. equi* challenge in a susceptible animal such as the mouse. Our method comprises the steps of preparing serial dilutions of a known amount of group C streptococcal organisms, adding those separate dilutions to aliquots of the blood serum sample and then incubating each sample under conditions sufficient to form immunochemical reaction complexes. Separate groups of susceptible animals are then inoculated with the above reaction complexes and the animals are observed for a period of time sufficient to determine the effects of the inoculates in each group of animals. These observations are then related to a standard to determine the antibody titers of the serum sample. In preferred embodiments, the group C streptococcal organism is an equine group C organism (i.e. *Strep. equi*) and the susceptible test animal in the mouse. The initial incubation steps are preferably at about 4° C. for about 60 minutes and the inoculated animals are observed over a period of at least about 68–72 hours at which time $LD_{50}$ determinations are made and then used, with a standard, to determine the group C streptococcal antibody titer in the original serum sample.

SPECIFIC EMBODIMENTS

Although in principle our assay should work using any group C susceptible test animal, in practice we use the mouse and our illustrative example below utilized that animal. Our test can be referred to simply as a mouse protection test procedure for determining group C streptococcal antibody titer in serum.

EXAMPLE (Mouse Protection Test Procedure)

OBJECTIVE: To measure serological antibody levels to *S. equi.* in horses.

MATERIALS:
1. 3.9 cc or 10 cc vials, 30 cc or 50 cc vials
2. 18/25 gram CF-1 mice
3. 3 cc syringes with $22 \times \frac{3}{4}''$ needles
4. Todd Hewitt broth
5. 50% dextrose solution
6. 300 cc culture flasks
7. *S. equi* seed culture METHOD:
1. Serum to be tested is dispensed into 3.9 cc or 10 cc vials, 1.5 cc per vial. Vials are labelled according to the culture dilutions to be run. Usually 5 10-fold dilutions are run.
2. *S. equi* culture is started night before needed in Todd Hewitt broth+1% dextrose, and grown at 37° C. with shaking.
3. The *S. equi* overnight culture is then passaged into Todd Hewitt broth+1% dextrose, a 10% inoculum, incubated at 37° C. with shaking for approximately 2 hours to an $O.D._{540}$ 0.9–1.0.
4. The *S. equi* culture at $O.D._{540}$ 0.9–1.0 is diluted 10-fold in Todd Hewitt broth to obtain dilutions desired (dilutions vary with sera being run, ranging from $10^{-2}$ to $10^{-8}$).
5. Culture dilutions are dispensed into corresponding vials containing serum, using about 1.5 cc of culture dilution per vial.
6. Vials containing serum/culture mixture are rim-sealed and incubated at 4° C. for 60 minutes.
7. Serum/culture mixtures are removed from the 4° C. incubator after 60 minutes, placed in ice, and then used to inoculate mice. Five mice are inoculated at each culture dilution, with 0.5 cc serum/culture mixture injected intraperitoneally (IP) into each mouse.
8. The mice are observed for 68–72 hours post inoculation and number dead recorded on cage cards. At the end of 68–72 hours, final observations are made and cards removed from cages.

CALCULATIONS:
1. Number of dead mice are recorded for each culture dilution on each serum.
2. $LD_{50}$ is calculated using the Reed-Muench method for 50% endpoint.

EXAMPLE

| Horse # | $10^{-3}$ | $10^{-4}$ | $10^{-5}$ | $10^{-6}$ | $10^{-7}$ | $LD_{50}$ | |
|---|---|---|---|---|---|---|---|
| 1 | 5/5* | 1/5 | 0/5 | 0/5 | 0/5 | $10^{3.6}$ | = seropositive |
| 2 | 5/5 | 5/5 | 5/5 | 5/5 | 0/5 | $10^{6.5}$ | = seronegative |

*recorded as dead/total

It should be understood that the above example is merely illustrative and that our method is subject to numerous variations that, given this disclosure, will become apparent to those skilled in the art. Accordingly, it is intended that the inventions disclosed herein should be limited only by the following claims.

We claim:

1. A method for determining the titer of antibodies to a *Streptococcus equi* organism in an equine blood serum sample, the method comprising the steps of:
   (a) preparing serial dilutions of a known amount of *Streptococcus equi* organisms;
   (b) adding the serial dilutions of step (a) to aliquots of the blood serum sample;
   (c) incubating each sample under conditions sufficient to form immunochemical reaction complexes;
   (d) preparing an inoculate with the reaction complexes of step (c) and inoculating separate groups of mice with the reaction complexes of step (c); and
   (e) observing the inoculated mice for a period of time sufficient to determine the effects of the inoculates in each group of mice and relating those observations to a standard to determine the antibody titer of the serum sample.

2. The method of claim 1 wherein the incubations of step (c) are at about 4° for about 60 minutes.

3. The method of claim 1 wherein the observation of step (e) is over a period of at least about 68–72 hours.

4. The method of claim 1 wherein the determinations of step (e) include determining $LD_{50}$ in the mice.

* * * * *